(12) United States Patent
Raz et al.

(10) Patent No.: US 8,162,814 B2
(45) Date of Patent: Apr. 24, 2012

(54) METHODS AND APPARATUS FOR CORRECTION OF URINARY AND GYNECOLOGICAL PATHOLOGIES, INCLUDING TREATMENT OF MALE INCONTINENCE, AND FEMALE CYSTOCELE

(75) Inventors: Shlomo Raz, Los Angeles, CA (US); Mordechay Beyar, Caesarea (IL); Oren Globerman, Herzelia (IL)

(73) Assignee: AMS Research Corporation, Minnetonka, MN (US)

( * ) Notice: Subject to any disclaimer, the term of this patent is extended or adjusted under 35 U.S.C. 154(b) by 642 days.

(21) Appl. No.: 12/346,080

(22) Filed: Dec. 30, 2008

(65) Prior Publication Data

US 2009/0143637 A1 Jun. 4, 2009

Related U.S. Application Data

(60) Continuation of application No. 10/625,199, filed on Jul. 23, 2003, now Pat. No. 7,608,036, which is a division of application No. 10/252,179, filed on Sep. 23, 2002, now Pat. No. 6,691,711, which is a division of application No. 09/748,963, filed on Dec. 27, 2000, now Pat. No. 6,502,578, which is a continuation of application No. 09/296,735, filed on Apr. 22, 1999, now Pat. No. 6,382,214.

(60) Provisional application No. 60/082,905, filed on Apr. 24, 1998.

(51) Int. Cl.
*A61F 2/02* (2006.01)

(52) U.S. Cl. ......................................................... 600/30

(58) Field of Classification Search ............... 600/29–32, 600/37; 128/897–898
See application file for complete search history.

(56) References Cited

U.S. PATENT DOCUMENTS

| 2,738,790 A | 3/1958 | Todt et al. |
| 3,182,662 A | 5/1965 | Shirodkar |
| 3,789,828 A | 2/1974 | Schulte |
| 3,995,619 A | 12/1976 | Glatzer |
| 4,172,458 A | 10/1979 | Pereyra |
| 4,452,245 A | 6/1984 | Usher |
| 4,509,516 A | 4/1985 | Richmond |
| 4,857,041 A | 8/1989 | Annis et al. |

(Continued)

FOREIGN PATENT DOCUMENTS

DE 2305815 2/1973

(Continued)

OTHER PUBLICATIONS

Aldridge, Albert H., B.S., M.D., F.A.C.S., Transplantation of Fascia for Relief of Urinary Stress Incontinence, American Journal of Obstetrics and Gynecology, v. 44, pp. 398-411, (1948).

(Continued)

*Primary Examiner* — Samuel Gilbert
(74) *Attorney, Agent, or Firm* — Kimberly K. Baxter; Gregory L. Koeller

(57) ABSTRACT

The present invention relates to apparatus and methods for treatment of male incontinence and a method for female cystocele repair in which a sling material is positioned between the descending rami of the pubic bone. In such an operation a "hammock-like" sling material is positioned below the urethra in males, or below the posterior bladder wall in the case of cystocele in females.

18 Claims, 9 Drawing Sheets

U.S. PATENT DOCUMENTS

| | | | |
|---|---|---|---|
| 4,873,976 A | 10/1989 | Schrelber | |
| 4,979,956 A | 12/1990 | Silvestrinl | |
| 5,013,292 A | 5/1991 | Lemay | |
| 5,019,032 A | 5/1991 | Robertson | |
| 5,032,508 A | 7/1991 | Naughton et al. | |
| 5,041,129 A | 8/1991 | Hayhurst et al. | |
| 5,053,043 A | 10/1991 | Gottesman et al. | |
| 5,085,661 A | 2/1992 | Moss | |
| 5,112,344 A | 5/1992 | Petros | |
| 5,188,636 A | 2/1993 | Fedotov | |
| 5,281,237 A | 1/1994 | Gimpelson | |
| 5,324,308 A | 6/1994 | Pierce | |
| 5,328,077 A | 7/1994 | Lou | |
| 5,337,736 A | 8/1994 | Reddy | |
| 5,362,294 A | 11/1994 | Seitzinger | |
| 5,383,904 A | 1/1995 | Totakura et al. | |
| 5,413,598 A | 5/1995 | Moreland | |
| 5,439,467 A | 8/1995 | Benderev et al. | |
| 5,443,449 A * | 8/1995 | Buelna | 604/105 |
| 5,501,695 A | 3/1996 | Anspach, Jr. et al. | |
| 5,520,700 A | 5/1996 | Beyar et al. | |
| 5,527,342 A | 6/1996 | Pietrzak et al. | |
| 5,544,664 A | 8/1996 | Benderev et al. | |
| 5,562,689 A | 10/1996 | Green et al. | |
| 5,571,139 A | 11/1996 | Jenkins, Jr. | |
| 5,582,616 A | 12/1996 | Bolduc et al. | |
| 5,591,163 A | 1/1997 | Thompson | |
| 5,611,515 A | 3/1997 | Benderev et al. | |
| 5,626,614 A * | 5/1997 | Hart | 606/232 |
| 5,647,836 A * | 7/1997 | Blake et al. | 600/30 |
| 5,683,349 A | 11/1997 | Makower et al. | |
| 5,807,403 A | 9/1998 | Beyar et al. | |
| 5,836,314 A | 11/1998 | Benderev et al. | |
| 5,836,315 A | 11/1998 | Benderev et al. | |
| 5,842,478 A | 12/1998 | Benderev et al. | |
| 5,843,099 A * | 12/1998 | Nichols et al. | 606/144 |
| 5,860,425 A | 1/1999 | Benderev et al. | |
| 5,899,909 A | 5/1999 | Claren et al. | |
| 5,904,692 A | 5/1999 | Steckel et al. | |
| 5,934,283 A | 8/1999 | Willem et al. | |
| 5,941,439 A | 8/1999 | Kammerer | |
| 5,944,732 A | 8/1999 | Raulerson et al. | |
| 5,972,000 A | 10/1999 | Beyar et al. | |
| 5,988,171 A | 11/1999 | Sohn et al. | |
| 5,997,554 A | 12/1999 | Thompson | |
| 6,010,447 A | 1/2000 | Kardjian | |
| 6,030,393 A | 2/2000 | Corlew | |
| 6,039,686 A | 3/2000 | Kovac | |
| 6,042,534 A * | 3/2000 | Gellman et al. | 600/30 |
| 6,042,536 A | 3/2000 | Tihon et al. | |
| 6,042,583 A | 3/2000 | Thompson et al. | |
| 6,053,935 A | 4/2000 | Brenneman et al. | |
| 6,077,216 A | 6/2000 | Benderev et al. | |
| 6,110,101 A | 8/2000 | Tihon et al. | |
| 6,117,067 A | 9/2000 | Gil-Vernet | |
| 6,127,597 A | 10/2000 | Beyar et al. | |
| 6,168,611 B1 | 1/2001 | Risvi | |
| 6,273,852 B1 | 8/2001 | Lehe et al. | |
| 6,322,492 B1 | 11/2001 | Kovac | |
| 6,328,686 B1 | 12/2001 | Kovac | |
| 6,334,446 B1 | 1/2002 | Beyar | |
| 6,382,214 B1 | 5/2002 | Raz et al. | |
| 6,406,423 B1 | 6/2002 | Scetbon | |
| 6,423,080 B1 | 7/2002 | Gellman et al. | |
| 6,478,727 B2 | 11/2002 | Scetbon | |
| 6,502,578 B2 | 1/2003 | Raz et al. | |
| 6,575,984 B2 | 6/2003 | Beyar | |
| 6,575,998 B2 | 6/2003 | Beyar | |
| 6,592,610 B2 | 7/2003 | Beyar | |
| 6,599,235 B2 | 7/2003 | Kovac | |
| 6,612,977 B2 | 9/2003 | Staskin et al. | |
| 6,638,210 B2 | 10/2003 | Berger | |
| 6,638,211 B2 | 10/2003 | Suslian et al. | |
| 6,641,524 B2 | 11/2003 | Kovac | |
| 6,641,525 B2 | 11/2003 | Rocheleau et al. | |
| 6,652,450 B2 | 11/2003 | Neisz et al. | |
| 6,663,642 B2 | 12/2003 | Beyar et al. | |
| 2001/0049467 A1 | 12/2001 | Lehe et al. | |
| 2001/0053916 A1 | 12/2001 | Rioux | |
| 2002/0007222 A1 | 1/2002 | Desal | |
| 2002/0035369 A1 | 3/2002 | Beyar et al. | |
| 2002/0055748 A1 | 5/2002 | Gellman et al. | |
| 2002/0058959 A1 | 5/2002 | Gellman | |
| 2002/0077526 A1 | 6/2002 | Kammerer et al. | |
| 2002/0095181 A1 | 7/2002 | Beyar | |
| 2002/0099259 A1 | 7/2002 | Anderson et al. | |
| 2002/0128670 A1 | 9/2002 | Ulmsten et al. | |
| 2002/0138025 A1 | 9/2002 | Gellman et al. | |
| 2002/0147382 A1 | 10/2002 | Neisz et al. | |
| 2002/0151909 A1 | 10/2002 | Gellman et al. | |
| 2002/0151910 A1 | 10/2002 | Gellman et al. | |
| 2002/0156487 A1 | 10/2002 | Gellman et al. | |
| 2002/0156488 A1 | 10/2002 | Gellman et al. | |
| 2002/0156489 A1 | 10/2002 | Gellman et al. | |
| 2003/0023136 A1 | 1/2003 | Raz et al. | |
| 2003/0062052 A1 | 4/2003 | Carter et al. | |

FOREIGN PATENT DOCUMENTS

| | | |
|---|---|---|
| DE | 4220283 C2 | 5/1994 |
| EP | 0470308 A1 | 2/1992 |
| EP | 1093758 A1 | 10/2000 |
| SU | 1225547 A | 4/1986 |
| SU | 1342486 A1 | 10/1987 |
| WO | WO 93/17635 A1 | 9/1993 |
| WO | WO 93/19678 A2 | 10/1993 |
| WO | WO 98/19606 A1 | 5/1998 |
| WO | WO 98/35616 A1 | 8/1998 |
| WO | WO 99/37217 A1 | 7/1999 |
| WO | WO 99/58074 A2 | 11/1999 |
| WO | WO 00/18319 A1 | 4/2000 |
| WO | WO 00/40158 A2 | 7/2000 |
| WO | WO 00/57812 A1 | 10/2000 |
| WO | WO 00/64370 A1 | 11/2000 |
| WO | WO 00/74594 A1 | 12/2000 |
| WO | WO 00/74613 A1 | 12/2000 |
| WO | WO 00/74633 A2 | 12/2000 |
| WO | WO 01/26581 A1 | 4/2001 |
| WO | WO 01/45569 A1 | 6/2001 |
| WO | WO 01/56499 A1 | 8/2001 |
| WO | WO 02/28312 A1 | 4/2002 |
| WO | WO 02/32284 A2 | 4/2002 |
| WO | WO 02/34124 A2 | 5/2002 |
| WO | WO 02/39890 A2 | 5/2002 |
| WO | WO 02/071953 A2 | 9/2002 |

OTHER PUBLICATIONS

Araki, Tohru, et al., The Loop-Loosening Procedure for Urination Difficulties After Stamey Suspension of the Vesical Neck, The Journal of Urology, vol. 144, pp. 319-323 (Aug. 1990).

Asmussen, M., et al., Simultaneous Urethro-Cystometry With a New Technique, Scand J Urol Nephrol 10, p. 7-11 (1976).

Benderev, Theodore, Anchor Fixation and Other Modifications of Endoscopic Bladder Neck Suspension, Urology, vol. 40, No. 5, pp. 409-418, (Nov. 1992).

Bergman, Arieh, et al., Three Surgical Procedures for Genuine Stress Incontinence: Five-Year Follow-up of a Prospective Randomized Study, Am J Obstet Gynecol, vol. 173 No. 1, pp. 66-71 (Jul. 1995).

Blaivas, Jerry, Commentary: Pubovaginal Sling Procedure Surgery for Female Incontinence, pp. 93-100 (1999).

Blaivas, Jerry, et al., Pubovaginal Fascial Sling for the Treatment of Complicated Stress Urinary Incontinence, The Journal of Urology, vol. 145 (6), pp. 1214-1218 (Jun. 1991).

Blaivas, Jerry, et al., Type III Stress Urinary Incontinence: Importance of Proper Diagnosis and Treatment, Surgical Forum, pp. 473-475. (1984).

Bryan, Fred E., Marlex Gauze Hammock Sling Operation With Cooper's Ligament Attachment in the Management of Recurrent Urinary Stress Incontinence, American Journal of Obstetrics and Gynecology, vol. 133, pp. 292-294 (Feb. 1979).

Burch, John C., Urethrovaginal Fixation to Cooper's Ligament for Correction of Stress Incontinence, Cystocele, and Prolapse, Am. J. Obst. & Gyn, vol. 31, pp. 281-290 (1961).

Choe, Jong M., et al., Gore-Tex Patch Sling: 7 Years Later, Urology, vol. 54, pp. 641-646 (1999).

Cook/Ob Gyn®, Urogynecology, Copyright Cook Urological Inc., pp. 1-36 (1996).

Decter, Ross, Use of the Fascial Sling for Neurogenic Incontinence Lessons Learned, The Journal of Urology, vol. 150 pp. 683-686 (Aug. 1993).

DeLancey, John, MD, Structural Support of the Urethra as it Relates to Stress Urinary Incontinence: The Hammock Hypothesis, Am J Obstet Gynecol, vol. 170 No. 6, pp. 1713-1723 (Jun. 1994).

Enzelsberger, H., et al., Urodynamic and Radiologic Parameters Before and After Loop Surgery for Recurrent Urinary Stress Incontinence, Acta Obstet Gynecol Scand, 69, pp. 51-54 (1990).

Eriksen, Bjarne C., et al., Long-Term Effectiveness of the Burch Colposuspension in Female Urinary Stress Incontinence, Acta Obstet Gynecol Scand, 69, pp. 45-50 (1990).

Falconer, C., et al., Clinical Outcome and Changes in Connective Tissue Metabolism After Intravaginal Slingplasty in Stress Incontinence Women, International Urogynecology Journal, pp. 133-137 (1966).

Falconer, C., et al., Influence of Different Sling Materials of Connective Tissue Metabolism in Stress Urinary Incontinent Women, International Urogynecology Journal, Supp. 2, pp. S19-S23 (2001).

Gittes, Ruben, et al., No-Incision Pubovaginal Suspension for Stress Incontinence, The Journal of Urology, vol. 138, pp. 568-570 (Sep. 1987).

Handa et al, Banked Human Fascia Lata for the Suburethral Sling Procedure: A Preliminary Report, Obstetrics & Gynecology, vol. 88 No. 6, 5 pages (Dec. 1996).

Henriksson, L., et al., A Urodynamic Evaluation of the Effects of Abdominal Urethrocystopexy and Vaginal Sling Urethroplasty in Women With Stress Incontinence, Am. J. Obstet. Gynecol. vol. 131, No. 1, pp. 77-82 (Mar. 1, 1978).

Hodgkinson, C. Paul, et.al., Urinary Stress Incontinence in the Female, Department of Gynecology and Obstetrics, Henry Ford Hospital, vol. 10, No. 5, p. 493-499, (Nov. 1957).

Ingeiman-Sunberg, A., et al., Surgical Treatment of Female Urinary Stress Incontinence, Contr. Gynec, Obstet., vol. 10, pp. 51-69 (1983).

Jeffcoate, T.N.A, The Results of the Aldridge Sling Operation for Stress Incontinence, Journal of Obstetrics and Gynaecology, pp. 36-39 (1956).

Karram, Mickey, et al., Patch Procedure: Modified Transvaginal Fascia Lata Sling for Recurrent for Severe Stress Urinary Incontinence, vol. 75, pp. 461-463 (Mar. 1990).

Kersey, J., The Gauze Hammock Sling Operation in the Treatment of Stress Incontinence, British Journal of Obstetrics Gynecology, pp. 946-949 (Oct. 1983).

Klutke, John, M.D. et al, The promise of tension-free vaginal tape for female SUI, Contemporary Urology, 7 pages (Oct. 2000).

Korda, A., et al., Experience With Silastic Slings for Female Urinary Incontience, Aust NZ J. Obstet Gynaecol, vol. 29, pp. 150-154 (May 1989).

Leach, Gary E., Bone Fixation Technique for Transvaginal Needle Suspension, Urology, vol. XXXI, No. 5, pp. 388-390, (May 1988).

Lichtenstein, Irving L., et al, The Tension Free Hernioplasty, The American Journal of Surgery, vol. 157 pp. 188-193 (Feb. 1989).

Loughlin, Kevin, et al., Review of an 8-Year Experience With Modifications of Endoscopic Suspension of the Bladder Neck for Female Stress Incontinence, The Journal of Urology, vol. 143, pp. 44-45. (Jan. 1990).

Marshall, Victor Fray, et al. The Correction of Stress Incontinence by Simple Vesicourethral Suspension, Surgery, Gynecology and Obstetrics, vol. 88, pp. 509-518 (1949).

Mascio, Valenzio C., et al., Therapy of Urinary Stress Incontinence in Women Using Mitek Gil Anchors, Mitek Surgical Products brochure (1993).

McGuire, Edward J., M.D., Abdominal Procedures for Stress Incontinence. Urologic Clinics of North America, pp. 285-290, vol. 12, No. 2 (May 1985).

McGuire, Edward J., et al., Experience With Pubovaginal Slings for Urinary Incontinence at the University of Michigan, Journal of Urology, vol. 138, pp. 90-93(1987).

McGuire, Edward J., et al., Pubovaginal Sling Procedure for Stress Incontinence, The Journal of Urology, vol. 119, pp. 82-84 (Jan. 1978).

McIndoe, G. A., et al., The Aldridge Sling Procedure in the Treatment of Urinary Stress Incontinence, Aust N Z Journal of Obstet Gynecology, pp. 238-239 (Aug. 1987).

McKiel, Charles F., et al., Marshall-Marchette Procedure Modification, The Journal of Urology, vol. 96, pp. 737-739, (Nov. 1966).

Moir, J. Chesser, et,al., The Gauze-Hammock Operation, The Journal of Obstetrics and Gynaecology of British Commonwealth, vol. 75 No. 1, pp. 1-9 (Jan. 1966).

Morgan, J. E., A Sling Operation, Using Marlex Polypropylene Mesh, for the Treatment of Recurrent Stress Incontinence, Am. J. Obst. & Gynecol, pp. 369-377 (Feb. 1970).

Narik, G., et al., A Simplified Sling Operation Suitable for Routine use, Gynecological and Obstetrical Clinic, University of Vienna, vol. 84, No. 3, p. 400-405, (Aug. 1, 1962).

Nichols, David H., The Mersilene Mesh Gauze-Hammock for Severe Urinary Stress Incontinence, Obstetrics and Gynecology, vol. 41, pp. 88-93 (Jan. 1973).

Norris, Jeffrey P., et al., Use of Synthetic Material in Sling Surgery: A Minimally Invasive Approach, Journal of Endourology, vol. 10, pp. 227-230 (Jun. 1996).

O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).

Ostargerd, Donald R. et al., Urogynecology and Urodynamics Theory and Practice, pp. 569-579 (1996).

Pereyra, Armand J., M.D., F.A.C.S., A Simplified Surgical Procedure for Correction of Stress Incontinence in Women, West.J.Surg., Obst. & Gynec, p. 223-226, (Jul.-Aug. 1959).

Petros, Peter E. Papa, Development of Generic Models for Ambulatory Vaginal Surgery—Preliminary Report,International Urogynecology Journal, pp. 20-27 (1998).

Petros, Peter E. Papa, et al., An Analysis of Rapid Pad Testing and the History for the Diagnosis of Stress Incontinence, Acta Obstet Gynecol Scand, vol. 71, pp. 529-538 (1992).

Petros, Peter E. Papa, et al., An Anatomical Basis for Success and Failure of Female Incontinence Surgery, Scandinavian Journal of Neurourology and Urodynamica, Sup 153, pp. 55-60 (1993).

Petros, Peter E. Papa, et al., An Integral Theory of Female Urinary Incontinence, Acta Obstetricia at Gynecologica Scandinavica, vol. 69 Sup. 153, pp. 7-31 (1990).

Petros, Peter E. Papa, et al., Anchoring the Midurethra Restores Bladder-Neck Anatomy and Continence, The Lancet, vol. 354, pp. 997-998 (Sep. 18, 1999).

Petros, Peter E. Papa, et al., Bladder Instability in Women: A Premature Activation of the Micturition Reflex, Scandinavian Journal of Neurourology and Urodynamics, Sup 153, pp. 235-239 (1993).

Peter E. Papa, et al., Cough Transmission Ratio: An Indicator of Suburethral Vaginal Wall Tension Rather Than Urethral Closure?, Acta Obstet Gynecol Scand, vol. 69, Sup 153, pp. 37-39 (1990).

Petros, Peter E. Papa, et al., Cure of Stress Incontinence by Repair of External Anal Sphincter, Acta Obstet Gynecol Scand, vol. 69, Sup 153, p. 75 (1990).

Petros, Peter E. Papa, et al., Cure of Urge Incontinence by the Combined Intravaginal Sling and Tuck Operation, Acta Obstet Gynecol Scand, vol. 69, Sup 153, pp. 61-62 (1990).

Petros, Peter E. Papa, et al., Further Development of the Intravaginal Slingplasty Procedure—IVS III—(With Midline "Tuck"), Scandinavian Journal of Neurourology and Urodynamics, Sup 153, p. 69-71 (1993).

Petros, Peter E. Papa, et al., Medium-Term Follow-up of the Intravaginal Slingplasty Operation Indicates Minimal Deterioration of Urinary Continence With Time, (3 pages) (1999).

Petros, P. E. Papa, New Ambulatory Surgical Methods Using an Anatomical Classification of Urinary Dysfunction Improve Stress, Urge and Abnormal Emptying, Int. Urogynecology Journal Peivic Floor Dystfunctlon, vol. 8 (5), pp. 270-278, (1997).

Petros, Peter E. Papa, et al., Non Stress Non Urge Female Urinary Incontinence—Diagnosis and Cure: A Preliminary Report, Acta Obstet Gynecol Scand, vol. 69, Sup 153, pp. 69-70 (1990).

Petros, Peter E. Papa, et al., Part I: Theoretical, Morphological, Radiographical Correlations and Clinical Perspective, Scandinavian Journal of Neurourology and Urodynamics, Sup 153, pp. 5-28 (1993).

Petros, Peter E. Papa, et al., Part II: The Biomechanics of Vaginal Tissue and Supporting Ligaments With Special Relevance to the Pathogenesis of Female Urinary Incontinence, Scandinavian Journal of Neurourology and Urodynamics, Sup 153, pp. 29-40 plus cover sheet (1993).

Petros, Peter E. Papa, et al., Part III: Surgical Principles Deriving From the Theory, Scandinavian Journal of Neurourology and Urodynamics, Sup 153, pp. 41-52 (1993).

Petros, Peter E. Papa, et al., Part IV: Surgical Applications of the Theory—Development of the Intravaginal Sling Pklasty (IVS) Procedure, Scandinavian Journal of Neurourology and Urodynamics, Sup 153, pp. 53-54 (1993).

Petros, Peter E. Papa, et al., Pinch Test for Diagnosis of Stress Urinary Incontinence, Acta Obstet Gynecol Scand, vol. 69, Sup 153, pp. 33-35 (1990).

Petros, Peter E. Papa, et al., Pregnancy Effects on the Intravaginal Sling Operation, Acta Obstet Gynecol Scand, vol. 69, Sup 153, pp. 77-79 (1990).

Petros, Peter E. Papa, et al., The Autogenic Ligament Procedure: A Technique for Planned Formation of an Artificial Neo-Ligament, Acta Obstet Gynecol Scand, vol. 69, Sup 153, pp. 43-51 (1990).

Petros, Peter E. Papa, et al., The Combined Intravaginal Sling and Tuck Operation an Ambulatory Procedure for Cure of Stress and Urge Incontinence, Acta Obstet Gynecol Scand, vol. 69, Sup 153, pp. 53-59 (1990).

Petros, Peter E. Papa, et al., The Development of the Intravaginal Slingplasty Procedure: IVS II—(With Bilateral "Tucks"), Scandinavian Journal of Neurourology and Urodynamics, Sup 153, pp. 61-67 (1993).

Petros, Peter E. Papa, et al., The Free Graft Procedure for Cure of the Tethered Vagina Syndrome, Scandinavian Journal of Neurourology and Urodynamics, Sup 153, pp. 85-87(1993).

Petros, Peter E. Papa, et al., The Further Development of the Intravaginal Slingplasty Procedure—IVS V—(With "Double Breasted" Unattached Vaginal Flap Repair and Permanent Sling)., Scandinavian Journal of Neurourology and Urodynamics, Sup 153, pp. 77-79 (1993).

Petros, Peter E. Papa, et al., The Intravaginal Slingplasty Procedure: IVS VI—Further Development of the "Double Breasted" Vaginal Flap Repair—Attached Flap. Scandinavian Journal of Neurourology and Urodynamics, Sup 153, pp. 81-84 (1993).

Petros, Peter E. Papa, et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynarnics, Sup 153, pp. 89-93 (1993).

Petros, Peter E. Papa, et al., The Role of a LAX Posterior Vaginal Fornix in the Causation of Stress and Urgency Symptoms: A Preliminary Report, Acta Obstet Gynecol Scand, vol. 69, Sup 153, pp. 71-73 (1990).

Petros, Peter E. Papa, et al., The Tethered Vagina Syndrome, Post and Surgical Incontinence and I-Plasty Operation for Cure, Acta Obstet Gynecol Scand, vol. 69, Sup 153, pp. 63-67 (1990).

Petros, Peter E. Papa, et al., The Tuck Procedure: A Simplified Vaginal Repair for Treatment of Female Urinary Incontinence, Acta Obstet Gynecol Scand, vol. 69, Sup 153, pp. 41-42 (1990).

Petros, Peter E. Papa, et al., Urethral Pressure Increase on Effort Originates From Within the Urethra, and Continence From Musculovaginal Closure, Scandinavian Journal of Neurourology and Urodynamics, pp. 337-350 (1995).

Precision Tack, Transvaginal Anchor System, The Precise Approach to Transvaginal Sling Procedures (advertisement), Boston Scientific Corporation,Microvasive, 4 pages (Jun. 1998).

Precision Twist, Transvaginal Anchor System, Low Profile Design for Precise Anchor Placement (advertisement), Boston Scientific Corporation Microvasive 2 pages (Jun. 1998).

Rackley, Raymond R., M.D. et al. Tension-free Vaginal Tape and Percutaneous Vaginal Tape Sling Procedures,Techniques in Urology (2001), vol. 7, No. 2, pp. 90-100.

Rackley, Raymond, MD, Synthetic Slings: Five Steps for Successful Placement, Urology Times, p. 46,48,49 (Jun. 2000).

Raz, Shlomo, Female Urology, pp. 80-86, 369-398, 435-442 (1996).

Raz, Shlomo, Modified Bladder Suspension for Female Stress Incontinence, Urology, vol. XVII, No. 1, pp. 82-85, (Jan. 1981).

Richardson, David A., et al., Delayed Reaction to the Dacron Buttress Used in Urethropexy, The Journal of Reproductive Medicine, pages 689-692, vol. 29, No. 9 (Sep. 1984).

Ridley, John H., Appraisal of the Goebell-Frangenheim-Stoeckel Sling Procedure, Am, J. Obst. & Gyn., vol. 95, pp. 714-721 (Jul. 1966).

Roberts, Henry, M.D., Cystourethrography in Women, Deptment of Obstetrics and Gynaecology, University of Liverpool, vol. XXXV, No. 293, pp. 253-259 (May 1952).

Sloan, W.R., et al., Stress Incontinence of Urine: A Retrospective Study of the Complications and Late Results of Simple Suprapubic Suburethral Fascial Slings, The Journal of Urology, vol. 110, pp. 533-536 (Nov. 1973).

Spencer, Julia, et al., A Comparison of Endoscopic Suspension of the Vesical Neck With Suprapubic Vesicourethropexy for Treatment of Stress Urinary Incontinence, The Journal of Urology, vol. 137, pp. 411-415 (Mar. 1987).

Stamey, Thomas A., M.D., Endoscopic Suspension of the Vesical Neck for Urinary Incontinence in Females, Ann. Surg., vol. 192 No. 4, pp. 465-471 (Oct. 1980).

Stanton, Stuart, Suprapubic Approaches for Stress Incontinence in Women, Journal of American Gerfatio Society, vol. 38, pp. 351 (1990).

Stanton, Stuart, Springer-Veglag, Surgery of Female Incontinence, pp. 105-113 (1986).

Staskin, David R., et al., The Gore-Tex Sling Procedure for Female Sphincteric Incontinence: Indications, Technique, and Results, World Journal of Urology, vol. 15, pp. 295-299 (1997).

Studdiford, W.E., Transplantation of Abdominal Fascia for the Relief of Urinary Stress Incontinence, American Journal of Obstetrics and Gynecology, pp. 764-775 (1944).

TVT Tension-free Vaginal Tape, Gynecare, Ethicon, Inc., 23 pages (1999).

Ulmsten, Ulf, et al., A Multicenter Study of Tension-Free Vaginal Tape (TVT) for Surgical Treatment of Stress Urinary Incontinence, International Urogynecology Journal, vol. 9, pp. 210-213 (1998).

Ulmsten, Ulf, et al., A Three Year Follow up of Tension Free Vaginal Tape for Surgical Treatment of Female Stress Urinary Incontinence, British Journal of Obstetrics and Gynaecology, vol. 106, pp. 345-350 (1999).

Ulmsten, Ulf, et al., An Ambulatory Surgical Procedure Under Local Anesthesia for Treatment of Female Urinary Incontinence, International Urolgynecology Journal, vol. 7, pp. 81-86, (1996).

Ulmsten, Ulf, et al., Different Biochemical Composition of Connective Tissue in Continent, Acta Obstet Gynecol Scand, pp. 455-457 (1987).

Ulmsten, Ulf, et al., Intravaginal Slingplasty (IVS): An Ambulatory Surgical Procedure for Treatment of Female Urinary Incontinence, Scand J Urol Nephrol, vol. 29, pp. 75-82 (1995).

Ulmsten, Ulf, et al., The Unstable Female Urethra, Am. J. Obstet. Gynecol., vol. 144 No. 1, pp. 93-97 (Sep. 1, 1982).

Vesica® Percutaneous Bladder Neck Stabilization Kit, A New Approach to Bladder Neck Suspenison, Microvasive® Boston Scientific Corporation, 4 pages (1995).

Vesica® Sling Kits, Simplifying Sling Procedures, Microvasive® Boston Scientific Corporation, 4 pages (1998).

Walters, Mark D., Percutaneous Suburethral Slings: State of the Art, Presented at the conference of the American Urogynecologic Society, Chicago, 29 pages (Oct. 2001).

Webster, George, et al., Voiding Dysfunction Following Cystourethropexy: Its Evaluation and Management, The journal of Urology, vol. 144, pp. 670-673 (Sep. 1990).

Winter, Chester C., Peripubic Urethropexy for Urinary Stress Incontinence in Women, Urology, vol. XX, No. 4, pp. 408-411(Oct. 1982).

Woodside, Jeffrey R., et al., Suprapubic Endoscopic Vesical Neck Suspension for the Management of Urinary Incontinence in Myelodysplastic Girls, The Journal of Urology, vol. 135, pp. 97-99 (Jan. 1986).

Zacharin, Robert, et al., Pulsion Enterocele: Long-Term Results of an Abdominoperineal Technique, Obstetrics & Gynecology, vol. 55 No. 2, pp. 141-148 (Feb. 1980).

Zacharin, Robert, The Suspensory Mechanism of the Female Urethra, Journal of Anatomy, vol. 97, Part 3, pp. 423-427 (1963).

\* cited by examiner

METHODS AND APPARATUS FOR CORRECTION OF URINARY AND GYNECOLOGICAL PATHOLOGIES, INCLUDING TREATMENT OF MALE INCONTINENCE, AND FEMALE CYSTOCELE

CLAIM TO PRIORITY

The present application is a continuation application and claims priority to U.S. patent application Ser. No. 10/625,199, filed Jul. 23, 2003, which is a division of application Ser. No. 10/252,179, filed on Sep. 23, 2002, now U.S. Pat. No. 6,691,711, which is a division of application Ser. No. 09/748,963, filed on Dec. 27, 2000, now U.S. Pat. No. 6,502,578, which is a continuation of application Ser. No. 09/296,735, filed on Apr. 22, 1999, now U.S. Pat. No. 6,382,214.

FIELD OF THE INVENTION

The present invention relates to methods and devices for treatment of urinary pathologies.

BACKGROUND OF THE INVENTION

Male incontinence is a condition characterized by involuntary loss of urine, beyond the individual's control. One cause for this condition is damage to the urethral sphincter, such as can occur after prostatectomy, after radiation or after pelvic accidents. Other accepted reasons for male incontinence include bladder instability, over-flowing incontinence and fistulas.

The present application is directed to the treatment of male urinary incontinence which is related to urethral sphincter damage. Currently, the treatment of choice involves implantation of a Kaufman Prosthesis, an artificial sphincter (such as AMS-800), and a sling procedure in which a sling is inserted beneath the urethra and advanced in the retro pubic space, and perforating the abdominal fascia, such as in female sling procedures. See, Joseph J. Kaufman and Shlomo Raz, Urethral compression procedure for the treatment of male urinary incontinence, Journal of Urology 121: 605-608 (1979).

Cystocele is a condition in which, due to laxity of the pelvic floor, the bladder extrudes out and downwards. The severity of this bladder collapse is rated between grades 1-4. In grade four cystocele, the bladder extrudes out of the vaginal opening. The treatment of choice for this condition includes the reduction or closing of the pelvic floor opening from which the bladder descends using sutures.

As background to the inventions of the present application, further information is provided in the following publications, the disclosures of which are fully incorporated herein by reference: Eddie H. M. Sze, M.D and Mickey M. Karrara, M.D., Transvaginal repair of vault prolapse: a review, Obstetrics & Gynecology 89(3): 466-475 (1997); Shlomo Raz, M.D., Female Urology, Chapter 29 (Pathogenesis of Cystocele), Chapter 43 (Uterine Prolapse), Chapter 44 (Enterocele and Vault Prolapse); Joseph J. Kaufman and Shlomo Raz, Urethral compression procedure for the treatment of male urinary incontinence, Journal of Urology 121: 605608 (1979); Robert Cox and Peter H. L. Worth, Results of Treatment of Post-Prostatectomy Incontinence Using the Kaufman Prosthesis, Eur. Urol. 12: 154-157 (1986); Olavi A. Lukkarinen, Matti J. Kontturi, et al., Treatment of Urinary Incontinence with an Implantable Prosthesis, Scan. J. Urol. Nephrol. 23: 85-88 (1989); Sender Herschorn and Sidney B. Radomski, Fascial Slings and Bladder Neck Tapering in the Treatment of Male Neurogenic Incontinence, J. Urology 147: 1073-1075 (1992); Gene R. Barrett, M.D. Stephen H. Treacy, M.D. and Cynthia G. Ruff, M.D., Preliminary Results of the T-Fix Endoscopic Meniscus Repair Technique in an Anterior Cruciate Ligament Reconstruction Population, Arthroscopy: The Journal of Arthroscopic and Related Surgery, 13: 218-223 (1997).

SUMMARY OF THE INVENTION

In one embodiment, the present invention relates to apparatus and methods for treatment of male incontinence and a method for female cystocele repair in which a sling material is positioned between the descending rami of the pubic bone. In such an operation a "hammock-like" sling material is positioned below the urethra in males, or below the posterior bladder wall in the case of cystocele in females.

In the male case, this sling applies passive compression against the bulbar urethra. The compression, either by itself or in conjunction with urethral mobility, prevents urine leak during strain. If additional passive pressure is required on the urethra after surgery is completed, collagen or other bulky material can be injected with a tiny needle through the perineum, causing more pressure created by the bulky material held on one side (the lower side) by the sling, and on the other side compressing the urethra.

In another embodiment of the invention, an especially flat shaped balloon is positioned between the sling material and the urethra to provide desired compression. Examples of inflatable balloon devices are disclosed in the currently pending U.S. patent application Ser. No. 09/036,719 entitled Systems for Percutaneous Bone and Spinal Stabilization, Fixation and Repair, filed Mar. 6, 1998 by Mordechay Beyar, Oren Globerman and Elad Magal, the disclosure of which is fully incorporated herein by reference. This balloon is inflated with fluid, and the volume can be adjusted by inflation or reduction of the fluid inside the balloon, using a tiny needle inserted through the perineal area. In a further embodiment of the invention, the sling material is part of the flat balloon. The sling material and the balloon can either be an integral single unit, or the sling material can be attached or secured to the balloon. Inflation and deflation of the balloon, in conjunction with the sling (which is preferably secured using suitable bone anchors and suture), is used to correct the urinary pathology, in accordance with the methods disclosed herein. The sling is attached to the bone by means of bone anchors.

In another embodiment of the invention, T-anchors and anchor inserters are provided herein. The anchors and inserters are designed for use with gynecological and urological procedures, including, but not limited to, bladder neck suspension, sacrospinous ligament procedures for the treatment of vaginal vault prolapse, and sling procedures for the treatment of urinary stress incontinence and cystocele repair.

Further disclosure of the surgical procedures in the sling procedure are provided below.

DETAILED DESCRIPTION OF THE INVENTION AND THE PREFERRED EMBODIMENTS

Fascial "T-Anchors" for Sacrospinous Fixation

In accordance with the present invention, fascial anchor or screw devices are provided herein for fixation of soft tissue to soft tissue. These "T-Anchors" are positioned on a special delivery system, either straight or curved. They can be either absorbable or non-absorbable.

The anchors and inserters of the present inventions are designed for use with gynecological and urological procedures. The T-Anchor system is particularly designed for soft tissue fixation in sacrospinous ligament fixation procedures, for the treatment of vault prolapse, uterine prolapse, or prevention of vault prolapse. In such cases, the posterior wall of the vagina is opened, the sacrospinous ligament is palpated with a finger or is observed visibly, and the anchor (which is loaded on a long delivery system) is positioned on the sacrospinous ligament and pushed to perforate the ligament. Once perforated, the anchor is released, the delivery system is removed, and the suture is used to approximate the posterior vaginal wall and surrounding tissue. It is also possible to affix the suture, which is attached to an anchor positioned below the sacrospinous ligament, to the uterus.

Figure 1:
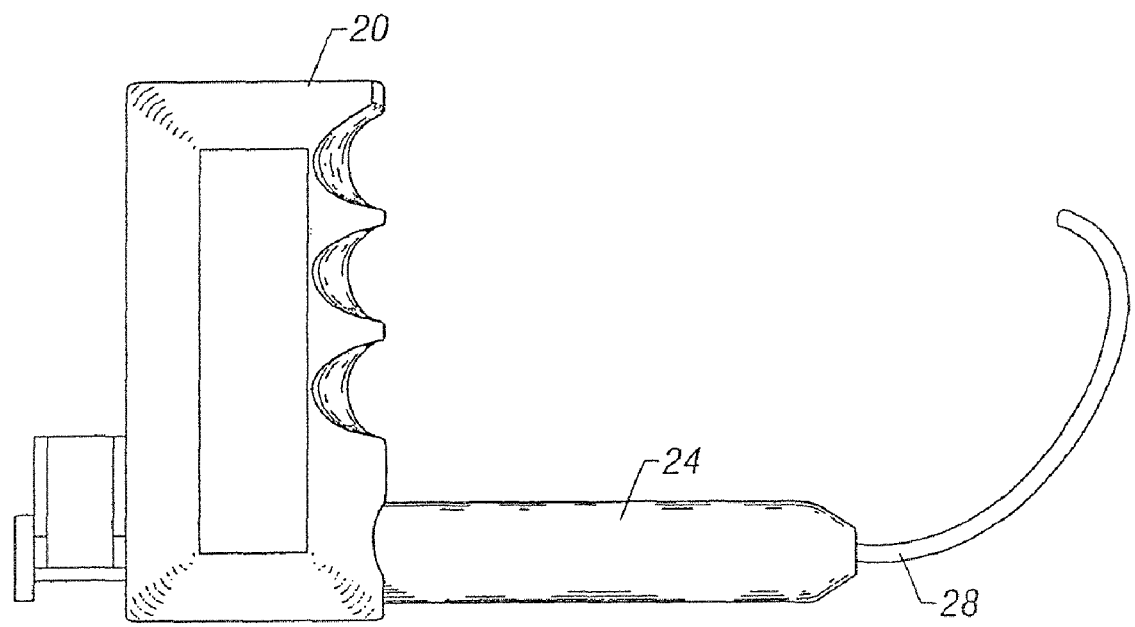
FIG. 1 is a plan view of a first embodiment of a T-inserter™, in accordance with the present invention.

One embodiment of the T-anchor inserter of the present invention is disclosed in FIG. 1. The anchor inserter is particularly designed for soft tissue fixation in bladder neck suspension and sling procedures for the treatment of urinary stress incontinence and for cystocele repair. The inserter has a handle 20 and a body 24. Body 24 extends perpendicular from handle 20. Extending from body 24 is tube or needle 28. Tube 28 is a curved anchor deployment tube, preferably constructed from stainless steel. The tube 28 is preferably of a narrow diameter such that it can be easily inserted into and manipulated within the vaginal canal for precise positioning of an anchor therein.

At the end of tube 28 is an anchor guide for holding an anchor, the anchor guide being at the distal end of the tube 28. In one embodiment of this guide, the outer end of the anchor guide can be formed as a thin-walled tube or bore, the bore receiving an anchor therein for securing the anchor to the inserter. In one preferred embodiment, the tube curves such that the end of the tube points back towards the inserter handle 20, or approximately to the handle of the inserter, and/or the distal end of the tube 28 is approximately parallel to the inserter body 24.

Handle 20 further includes a release button or trigger. Upon activation of the release button, the anchor is deployed from the inserter device. In the preferred embodiment, the anchor is designed for ejection from the inserter device to penetrate into soft tissue. The inserter is preferably constructed as a stainless steel tube 28 in which a plunger is positioned, such that upon pressing the release button, the plunger pushes the anchor out of the tube 28 and into the tissue. In addition to a release trigger, it is preferred that handle 20 further include a safety lock, to prevent premature ejection or release of the anchor.

In the preferred embodiment, straight anchors 32 are used with this inserter, each of the anchors being approximately 15 mm in length and 1.4 mm in diameter with a tapered end and a bore in the middle of the anchor for threading a suture thread therethrough. Each anchor is preferably made of Titanium or biocompatible plastic and is threaded through its bore with a non-absorbable suture such as braided polyester or polypropylene no. 0-1.

Figure 3:
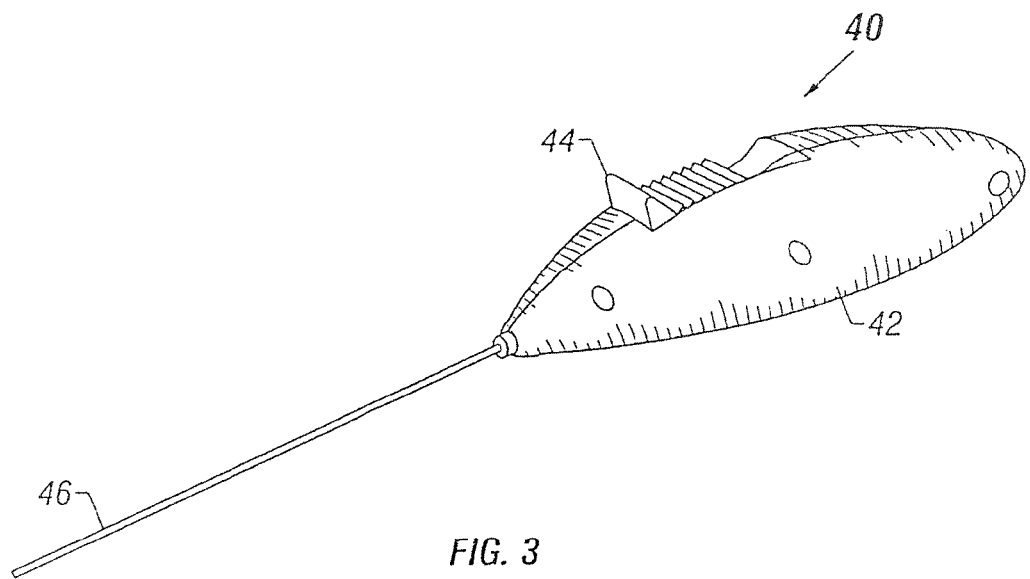
FIG. 3 is a plan view of a second embodiment of a T-inserter™, in accordance with the present invention.
Figure 9:
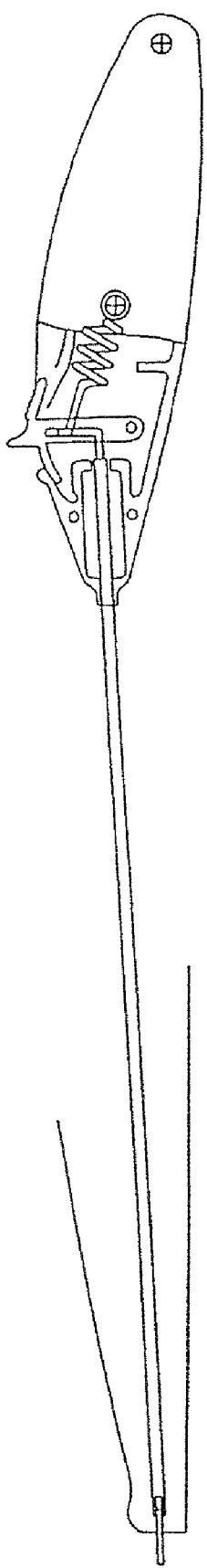
FIG. 9 is cross sectional view of the second embodiment of the T-inserter™, with the anchor having attached suture thread loaded thereon.

A second embodiment of the T-inserter of the present invention is shown in FIG. 3. This embodiment of the inserter is particularly designed for the sacrospinous ligament fixation procedures in accordance with the present invention. T-inserter 40 includes a handle 42 having a release button or trigger means 44. In the preferred embodiment, the T-inserter further includes a safety means for preventing accidental or premature release of an anchor from the T-inserter. Attached to the handle of the T-inserter is a straight tube or needle 46. At the end of tube 46 is an anchor guide for holding an anchor 48, the anchor guide being at the distal end of the tube, as shown in FIG. 9. In one embodiment of this guide, the outer end of the anchor guide can be formed with a bore, the bore receiving an anchor therein for securing the anchor to the inserter.

In the preferred embodiment, each of the anchors 48 for use with the T-inserter of FIG. 3 are approximately 11 mm in length and 1.5 mm in diameter, with a tapered end and a bore in the middle for threading the suture therethrough. The anchors are made of absorbable/resorbable materials such as Poly-1-lactide, and are threaded with an absorbable suture such as Vicryl suture no. 0-1.

Figure 5A:
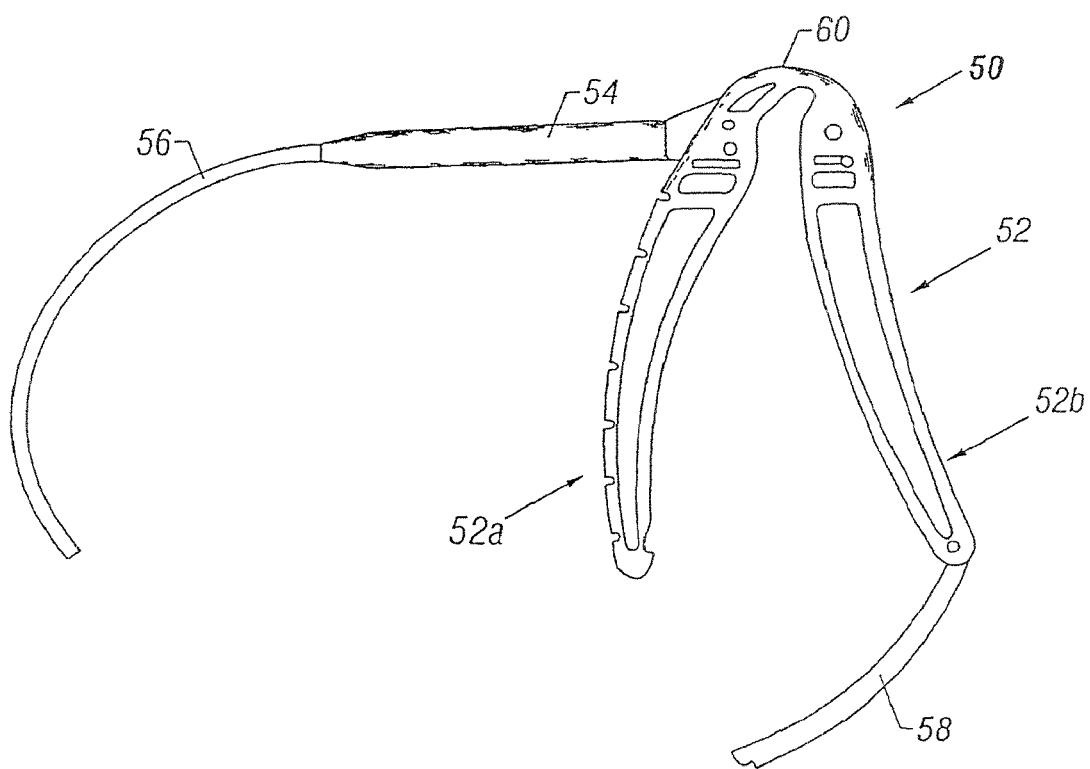
FIG. 5a-c are plan views of a third embodiment of a T-inserter™, in accordance with the present invention.
Figure 5B:
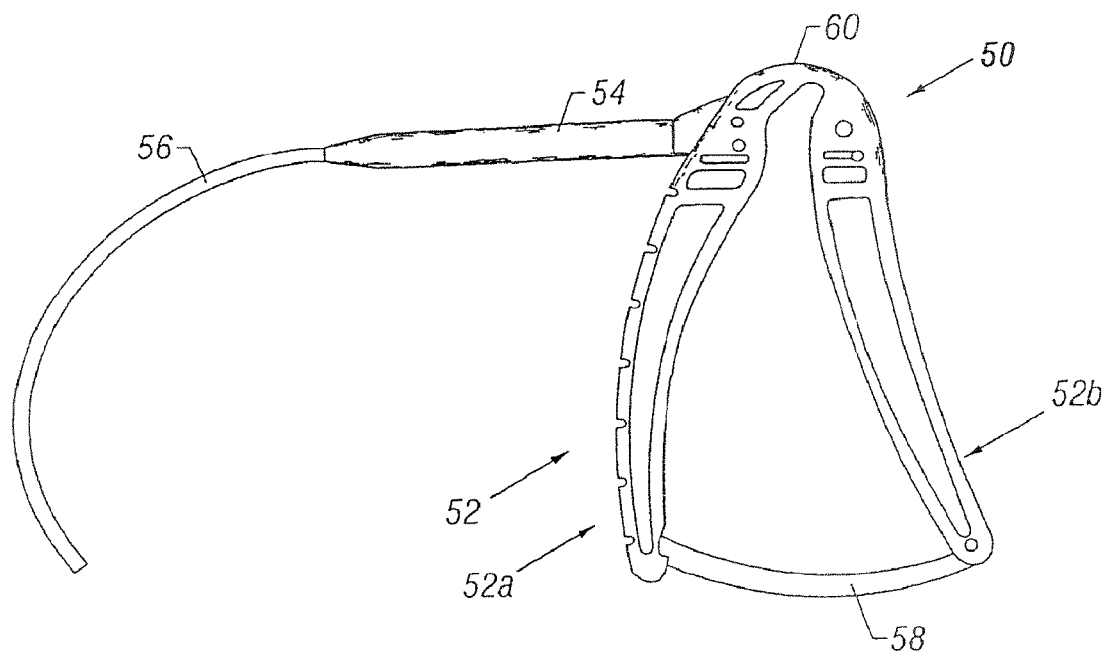
Figure 5C:
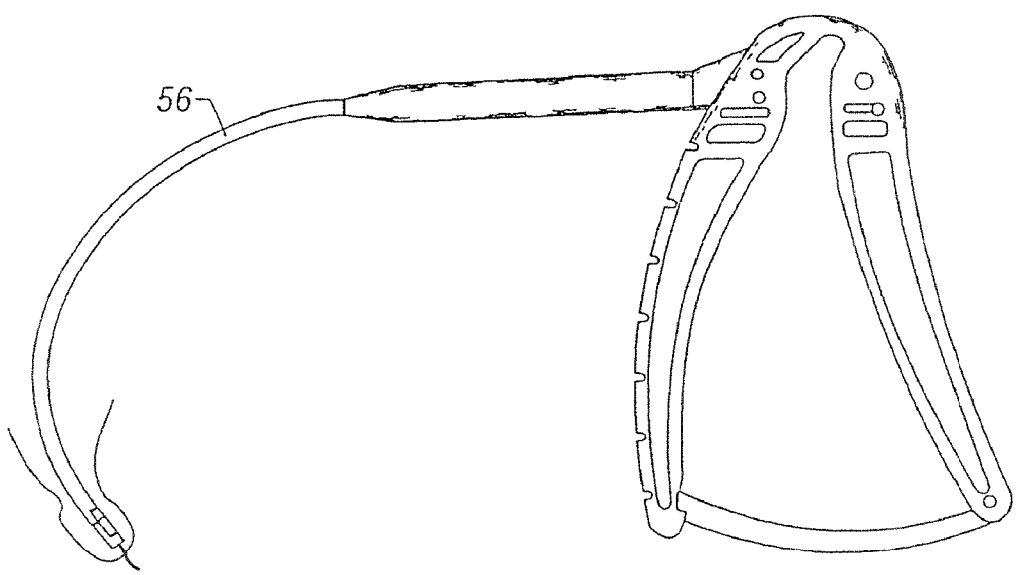
Figure 6:
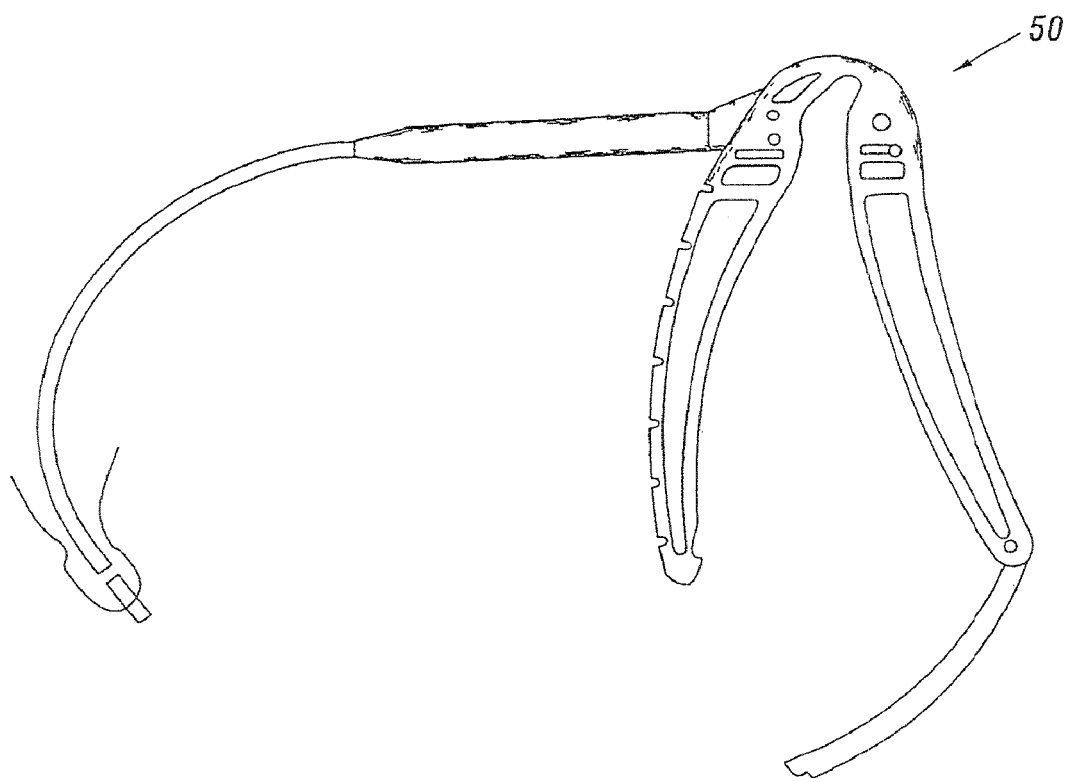
FIG. 6 is a plan view of the third embodiment of the T-inserter™, after release of a T-anchor# therefrom.

A further T-inserter 50, in accordance with the present invention, is shown in FIGS. 5 and 6. The T-inserter 50 includes a handle 52, a body 54, and a tube or needle 56. The inserter further includes a rigid segment or safety lock 58. This inserter is similar in its features to the inserters described above. In inserter 50, however, a different release technique is used. Handle 52 consists of a scissor or pincer like design in which handle 52 is separated into two separate segments or halves 52a and 52b, both connected at joint 60.

To use the inserter, an anchor with suture thread is inserted into the distal end of the tube 56, as described above. During the positioning of the inserter 50 within the body, safety lock 58 is kept in place to restrain handle segments 52a and 52b from movement, as shown in FIGS. 5b and 5c. When the inserter is in place, such that the distal end of tube 56 is correctly positioned with the distal end located at the proper point of anchor insertion, safety lock 58 is released as shown in FIG. 5a. Upon release of the safety lock 58, handle segments 52a and 52b can be squeezed together to cause a plunger to push through tube 56, pushing against the rear of an anchor to be released from the distal end of the inserter device, as shown in FIG. 6.

Figure 2:
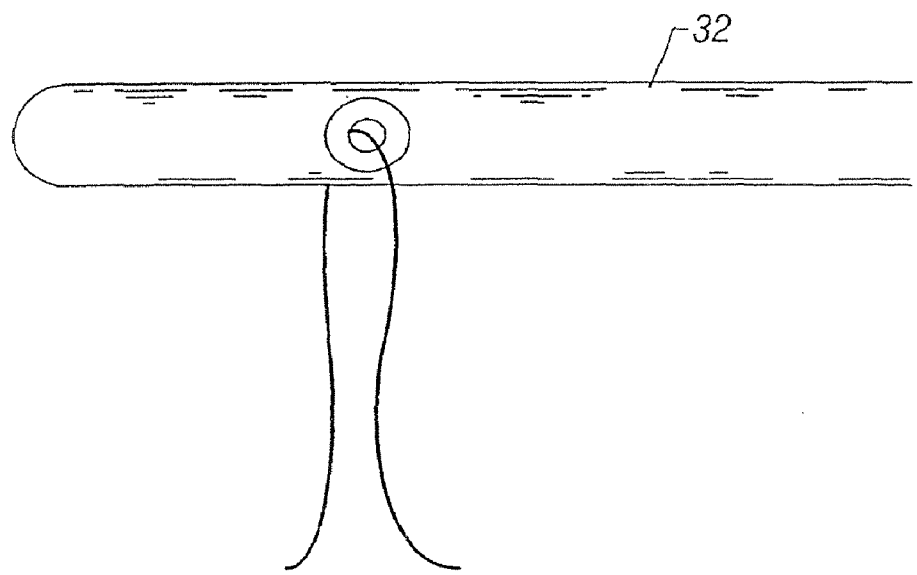
FIG. 2 is a plan view of a first embodiment of a T-anchor™, in accordance with the present invention.
Figure 4:
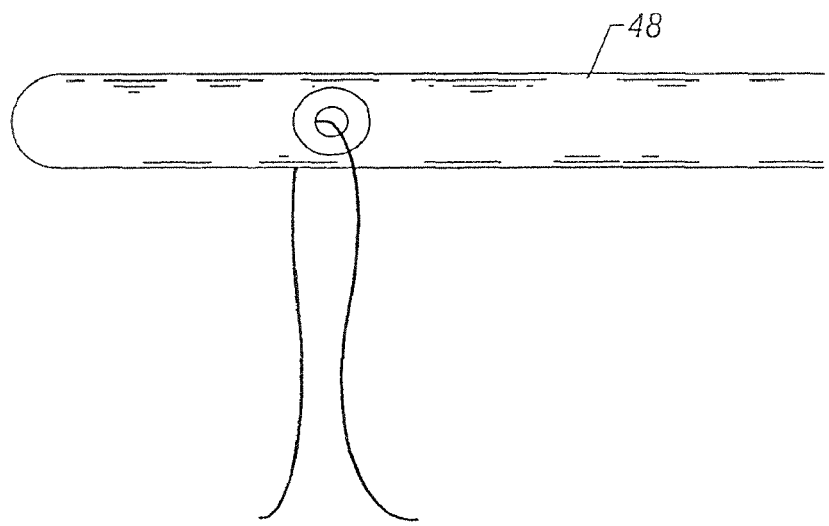
FIG. 4 is a plan view of a second embodiment of a T-anchor™, in accordance with the present invention.
Figure 7:
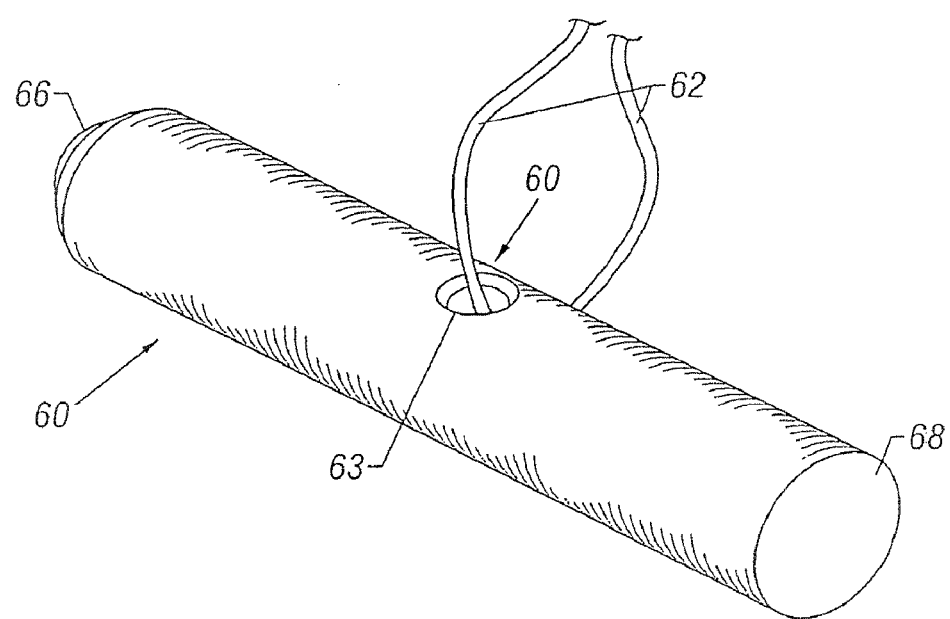
FIG. 7 is a perspective and enlarged view of a T-anchor™, in accordance with the present invention.

As described above, T-anchors for use in accordance with the present invention are disclosed in FIGS. 2 and 4. A further illustration of the T-anchor of the present invention is provided in FIG. 7. As shown in FIG. 7, anchor 60 consists of a basically cylindrical body 63 having a tapered end 66, a blunt end 68 and a bore 64 (in the preferred embodiment, extending perpendicularly to the longitudinal axis of the anchor) for receipt of a threaded suture 62 therethrough.

Figure 8B:
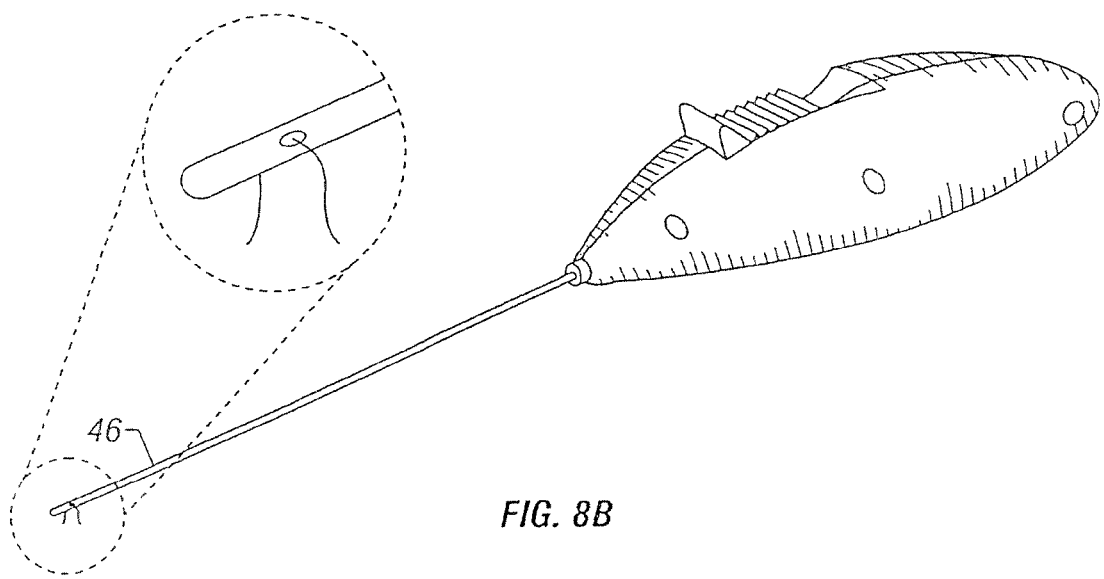
FIGS. 8a and 8b are plan views of the first and second embodiments of the T-inserter™, with the threaded anchor loaded into the tip of the inserter's tube up to the anchor's midpoint, so that the suture loop is located outside of the tube.
Figure 8A:
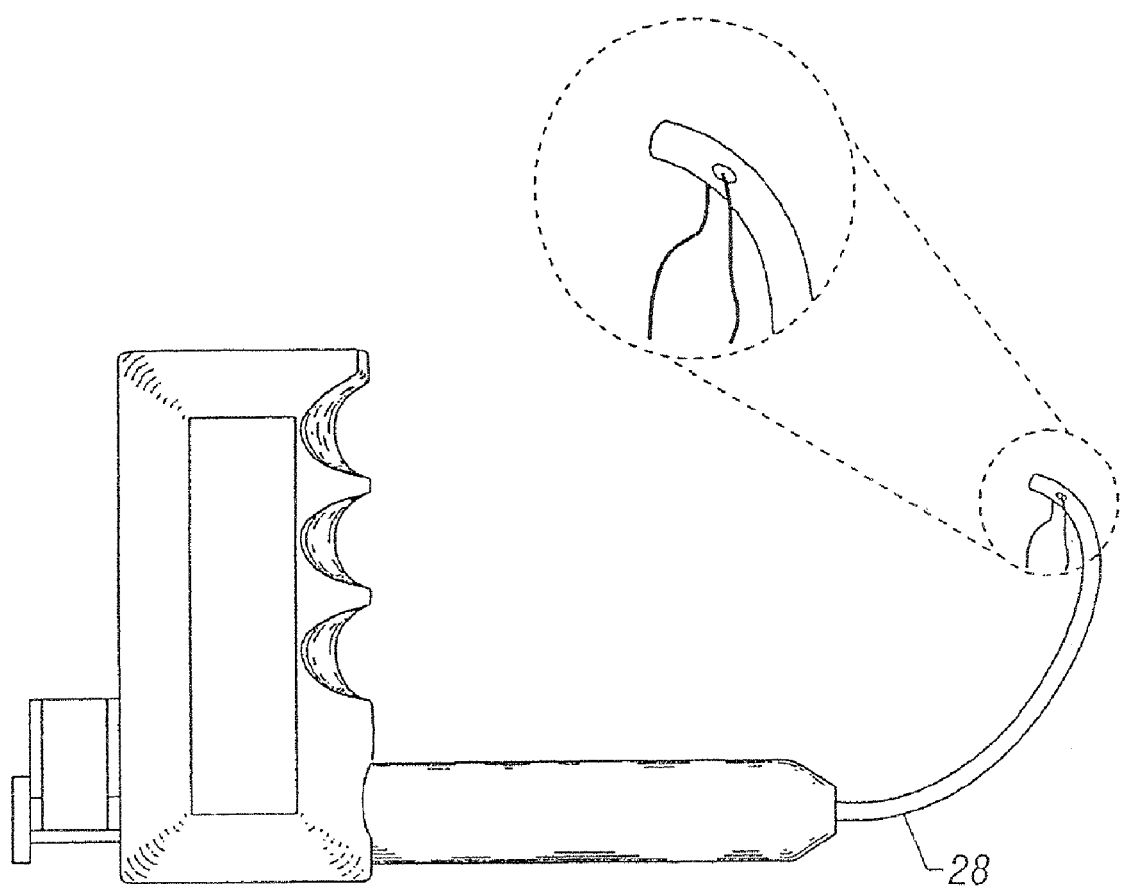

With the inserters of FIGS. 1, 3, and 5, and in accordance with the procedure of the present invention, approximately half the length of a suture is threaded through the bore of an anchor. As a result, the bore of the anchor, as shown in FIGS. 2, 4 and 7, sits midway on the strand of suture. Holding the threaded anchor at the tapered end 66, the blunt end of the anchor 68 is pressed into the bore at the tip of the inserter tube or needle. The threaded anchor is pushed backwardly into the tip of the inserter's needle up to the anchor's midpoint, so that the suture loop is outside of the tube 28, as shown in FIGS. 8a and 8b. Alternatively, the sides of the tube 28 can be provided with bayonet slots for accommodating the suture extending therethrough, with the anchor then being able to be fully recessed into the tube.

Bladder Neck Suspension Procedure with T-Anchor System

Figure 10:
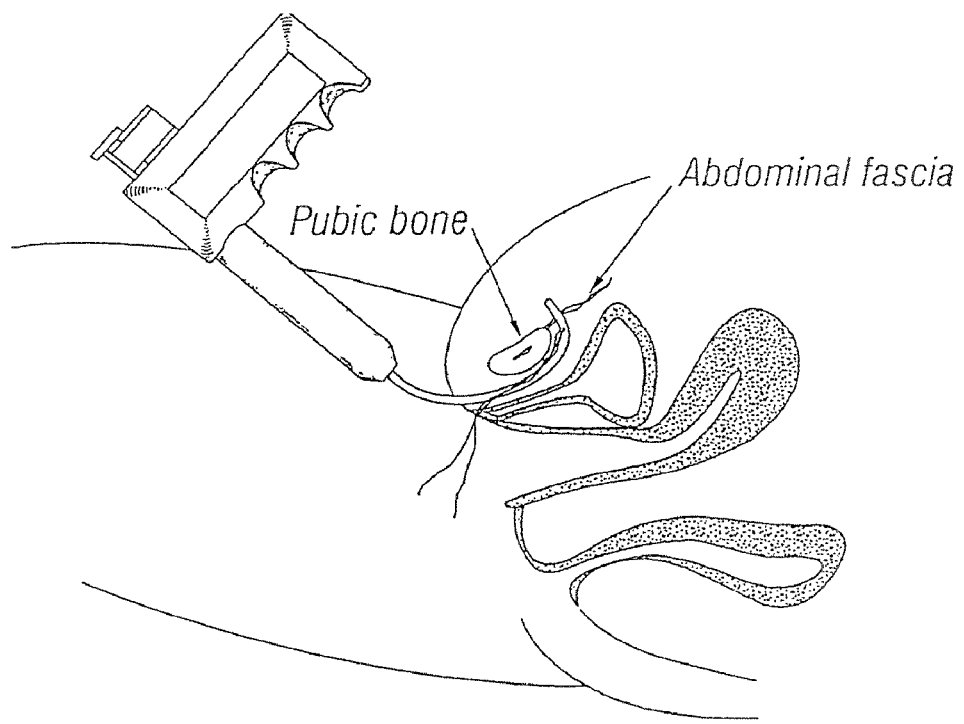
FIG. 10 is a sectional view showing the placement of a fascial anchor inserter and an anchor in accordance with the procedure for bladder neck suspension of the present invention.

In accordance with the invention, to perform a bladder neck suspension procedure, it is preferred that the anchor inserter of FIG. 1 be used. Once the patient has been placed under anesthesia, and is in the lithotomy position, a foley catheter is inserted into the bladder and the balloon is inflated. As shown in FIG. 10, the inserter is inserted through the anterior vaginal wall, lateral to the urethra, and is advanced along the posterior surface of the pubic bone, until the device's tip passes the abdominal fascia just above the superior pubic ramous. The safety lock on the inserter is then released, and the anchor is deployed, by pushing on the trigger of the inserter, into tissue. The inserter device is then removed from the vaginal canal, and the suture of the anchor is pulled to securely hold the anchor in the tissue. By pulling on the suture attached to the center of the anchor, the anchor assumes a parallel orientation relative to the fascial layer.

The procedure is then repeated on the contralateral side, and cystoscopy is performed to verify bladder and urethral integrity. At this point, anchor fixation to the abdominal fascia has been achieved and the vaginal suspension, using the free ends of the suture thread, is continued according to one of the procedures known in the art, including such procedures as the Raz, Pereyra, Gittes or sling procedure.

T-Sacrospinous Fixation Procedure

Figure 11:
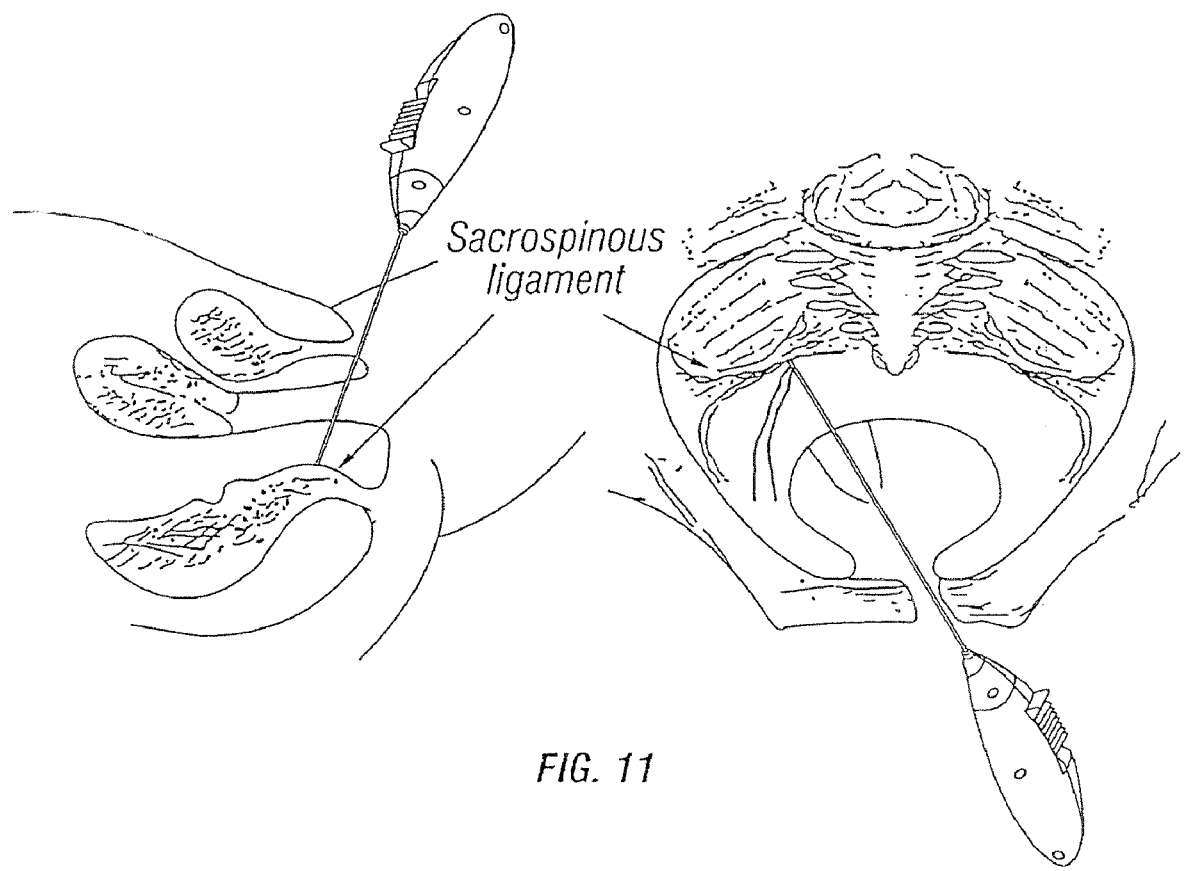
FIG. 11 shows two sectional views of the placement of a fascial anchor inserter and an anchor in accordance with the procedure for sacrospinous fixation of the present invention.

In accordance with the present invention, a T-Sacrospinous fixation procedure is further provided herein, as shown in FIG. 11. An T-anchor™ is threaded with suture and loaded onto the anchoring device of FIG. 3. With the patient under anaesthesia and in the lithotomy position, the surgical area and the vagina are disinfected. The posterior vaginal wall is opened, the rectum is pushed to the left, and the sacrospinous ligament is palpated. Palpating the ligament with a finger, the inserter is advanced along the finger until the tip of the anchor perforates the sacrospinous ligament. The insertion lever is then pressed (after disengaging the safety), causing the anchor to be deployed in the sacrospinous ligament, resulting in a firm attachment to the ligament. The inserter is then pulled out, and the suture is pulled for proper anchoring as disclosed above. The procedure is then repeated on the contralateral side. Colporrhaphy is then performed.

In accordance with additional inventions of the present application, a variety of further surgical procedures using bone screws to correct urological and gynecological pathologies are further disclosed below. The disclosures of U.S. patent application Ser. No. 08/1733,798 (filed Oct. 18, 1996) and Ser. No. 08/804,172 (filed Feb. 21, 1997), relating to bone anchors and inserters, including bone screw and screw inserters, are fully incorporated herein by reference.

Sling Procedure for Male Incontinence Using Pubic Bone Anchors

In accordance with one invention, a sling procedure is disclosed herein for treatment of male incontinence, and in particular for treatment of patients suffering from post-prostatectomy incontinence. For the procedure to be performed, the patient should have no urethral obstruction or any pathology involving the bulbar urethra. In this embodiment, bone anchors are used to suspend a sling material below the bulbomembranous urethra.

In accordance with the invention, the patient is first placed in the lithotomy position. After preparation and draping, a 16Fr. Foley catheter is inserted into the urethra, and the scrotum is elevated. A vertical incision is made over the midline in the perineum. The skin and subcutaneous tissues are dissected free. The bulbocavemous muscle is then exposed and dissection is carried out posteriorly to the area of the transverse perineum to completely free the bulbar urethra. Lateral dissection is used to expose the corpora cavernosum.

Upon exposure of the corpora cavernosum, four bone screws or anchors are inserted in the inner portion of the descending rami of the pubic bone using a straight screw or anchor inserter. Each bone screw is loaded with No. 1 Prolene sutures. The first pair of bone screws is inserted just below the symphysis, while the second pair is inserted at the level of the ischial tuberosity.

Figure 12:
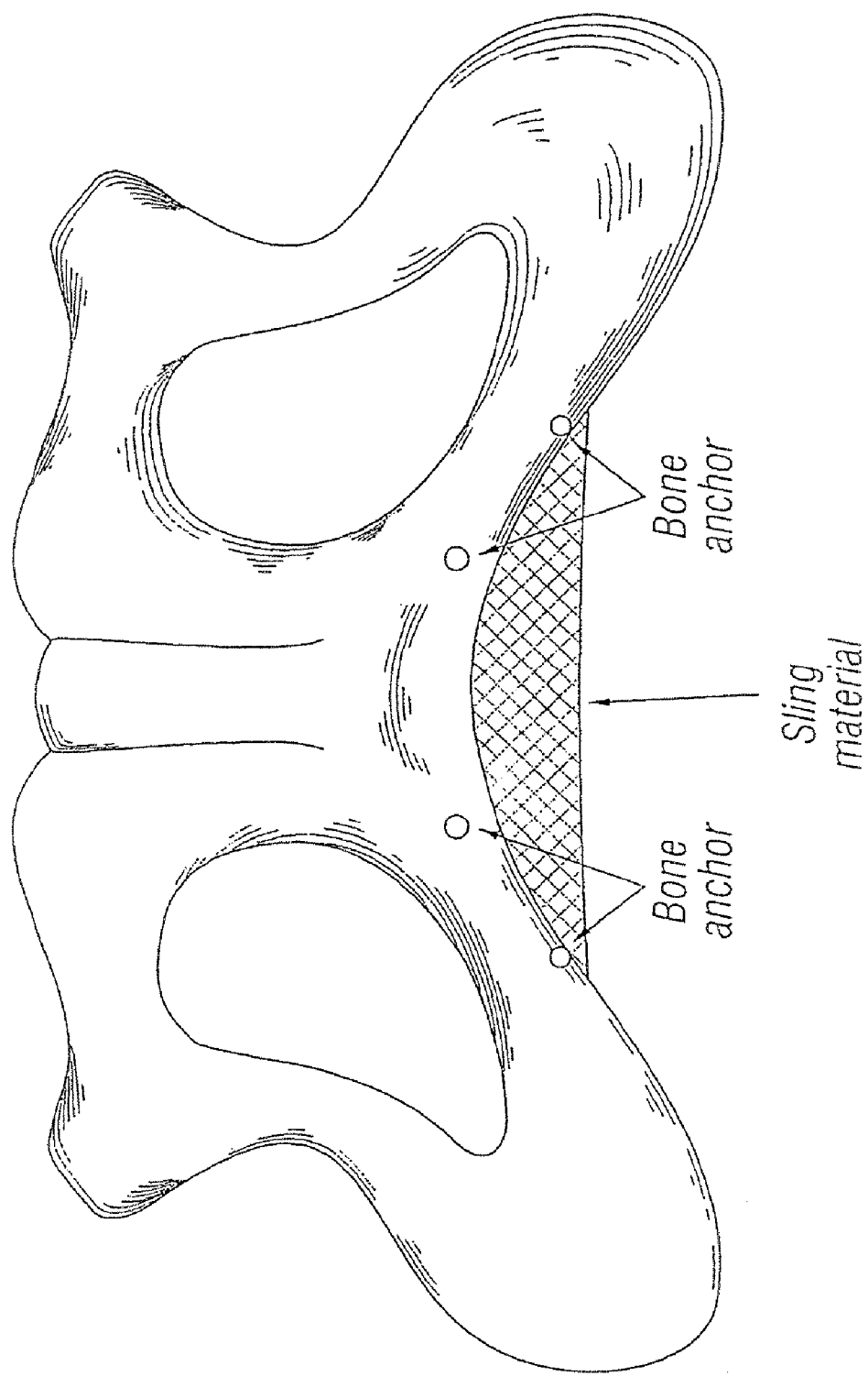
FIG. 12 is a view of an exposed pelvic bone showing the schematic location of the bone anchors and sling material using in a male sling procedure in accordance with the present invention.

When insertion of the second pair has been completed, a template is obtained from the bulbar urethral area and is measured. A segment of synthetic material or cadaveric or autologous fascia is fashioned over the template to create a sling. The four corners of the sling are then transfixed with the preloaded Prolene suture at each end. One side of the sling is tied tight over the pubic bone while in the contralateral side the tension will be adjusted. An example of the adjusted anatomy at this point, with the anchors and sling in place, is shown in FIG. 12.

The Foley catheter is then deflated and removed. The Foley catheter is connected to a sterile saline perfusion line. A zero pressure state is obtained by lowering the bag to the level of the symphysis. The tip of the catheter is repositioned at the penoscrotal angle and the urethral resistance to start the flow is recorded (by distance above the zero line). In patients under anesthesia suffering from sphincter incontinence, the resistance is very low. Tension is then applied to the untied side of the sling, and the pressure is adjusted to increase urethral resistance between 30 and 60 cm water. The second pair of sutures are then tied to the selected degree of tension.

The Foley catheter is then advanced to the bladder (which should advance without difficulties), and the wound is irrigated with Bethadine solution and closed in layers. Subsequently, the Foley catheter is removed after 2 hours, and the patient can be discharged home on oral antibiotics and pain medication.

Repair of Grade Four Cystocele Using Retropubic and Lateral Pubic Bone Anchors

In accordance with another invention of the present application, a method is provided for repair of cystocele using retropubic and lateral pubic bone anchors. This surgery is indicated for patients with grade four cystocele and urethral hypermobility. The procedure repairs the central defect, the lateral defect, approximates the cardinal ligaments to the midline, and creates a sling of the urethra.

After preparation and draping, a Foley catheter is inserted in the bladder. Once the catheter is in place, a "goal post" incision is made. The vertical bars of the goal post extend laterally from the distal urethra to the horizontal bar that is made just proximal to the bladder neck. The vertical bars reach the vaginal cuff.

After creation of the goal post incision, the vaginal wall is dissected free to expose the perivesical fascia laterally and the cardinal ligaments posteriorly. A figure eight 2-0 absorbable suture is applied to approximate the cardinal ligament to the midline without tying it. If an enterocele sac is encountered, it should be repaired at this stage.

The retropubic space is then entered over the periurethral fascia at the level of the vertical bars of the incision, and the urethropelvic ligaments are exposed. Two fascial anchors (the upper pair) are inserted into the tissue of the suprapubic area. Each of these anchors contains a preloaded No. 1 Prolene suture.

In an alternative embodiment, at this stage of the procedure, the retropubic space is not open and two bone anchors are applied to the inner surface of the symphisis using a right angle drill.

After application of the first set of anchors, a second pair of bone anchors or screws is applied to the inner surface of the descending rami of the symphysis. These anchors (the lower pair) also have No. 1 Prolene sutures preloaded in the bores of the screws.

Once the four anchors are in place, the bladder prolapse is reduced using a moist sponge over a right angle retractor. Alternatively, a Dexon mesh is applied and left in place. The lower pair of Prolene sutures are then used to incorporate the perivesical fascia and the cardinal ligaments area. Interrupted 2-0 absorbable sutures are used to approximate the perivesical fascia to the midline over the Dexon mesh.

The transverse segment of the goal post incision is then dissected free to create a groove or tunnel for the sling to be embedded or inlayed into. A synthetic rectangular sling or, alternatively, an autologous or cadaveric segment of fascia (of approximately 6 by 2 cm) is used to create the urethral sling. The end of the sling is transfixed with the upper pair of Prolene suture. Cystoscopy is performed after injection of indigocarmine to ensure ureteric patency, bladder integrity, and normal positioning of the sling.

Once the sling has been properly positioned, and ureteric patency and bladder integrity have been verified, the perivesical and cardinal ligament sutures are tied to close the central defect. The lateral defect suture is tied without tension.

The sling sutures are then tied over a cystoscope sheath at a 30 degree angle to avoid obstruction. The excess of the vaginal wall is excised, the vaginal wall is closed with running sutures, and a packing is inserted for 2 hours.

Transvaginal Repair of Enterocele Using Fascial Anchors

In a further invention, a procedure for transvaginal repair of enterocele using fascial anchors is provided herein.

In accordance with the invention, the patient is first placed in the lithotomy position. During preparation and draping, a rectal packing is inserted to facilitate the surgical procedure. A Foley catheter or suprapubic catheter is inserted to drain the bladder, and a ring retractor with six hooks is used to expose the vaginal canal.

The vaginal cuff is then held with Allis clamps and a vertical incision is made. The vaginal wall is dissected free, exposing the enterocele sac. The hooks of the ring retractor are used to hold the vaginal wall internally. Once the vaginal wall is securely held, the enterocele sac is dissected free, exposing posteriorly the pre rectal fascia and anteriorly the bladder wall. The enterocele sac is then opened, exposing the peritoneal contents. A large moist pad is inserted in the peritoneal cavity and a deep right angle retractor is used to elevate the anterior segment (bladder). The small bowel or distal colon is pushed away from the operating field.

A deep posterior retractor is then inserted posteriorly to displace the rectum laterally to the left side exposing the right pararectal area. By sliding a finger over this space, the soft levator musculature can be felt, and, just posteriorly, the hard surface of the coccigeus muscle and sacrospinous ligament, running from the ischial spine to the sacrum.

Using a straight fascial anchor and under finger control, two absorbable anchors are inserted through the right sacrospinous ligament 2-3 cm medial to the ischial spine. Each of the anchors are preloaded with suture, such that the sutures are threaded through the anchor, and can slide through the anchor freely when pulling on only one end. The strength and fixedness of each anchor's insertion is tested by a strong pull on both ends of the anchor's sutures.

At the deepest point of the vagina, one free end of the sutures is used for threading through a good sized portion of vaginal wall, and the end is then transferred to the vaginal lumen. Then the other end of the suture is likewise also transferred to the vaginal lumen, at a distance of approximately 1 to 2 cm from the prior suture.

Two sequential purse string sutures of No. 1 Vycryl are then used to close the peritoneal cavity. The suture includes the pre rectal fascia, the sacrouterine and cardinal ligaments, and the perivesical area. Alternatively, a Dexon mesh can be included with the last suture to reinforce the closure of the cul de sac. The sutures are tied and the excess of peritoneum is excised.

The pre rectal fascia is then closed using a running absorbable suture. The excess of vaginal wall is excised, and the vaginal wall closed with a running suture. The sacrospinous sutures are tied individually with the help of a right angle retractor, making sure that the vaginal dome slides tension to the anchoring point deep in the vagina.

A vaginal packing is then inserted for 2 hours and the patient can be discharged home after recuperation from anesthesia. Sling Procedure Using Fascial Anchors (Using Synthetic Material, Cadaveric or Autologous Fascia)

In a further invention, a sling procedure using fascial anchors (using synthetic material, cadaveric or autologous fascia) is provided herein. This technique is a vaginal sling procedure which provides treatment of stress incontinence in patients with minimal or mild urethral mobility (intrinsic sphincter deficiency).

In accordance with the invention, the patient is first placed under general, spinal or local anesthesia with controlled sedation. Once anesthetized, two oblique incisions are made in the anterior vaginal wall. The vaginal wall is dissected laterally over the periurethral fascia.

Using Mayo scissors and pointing toward the ipsilateral shoulder, the retropubic space is entered in each side. The urethropelvic pelvic ligament is detached creating a small window in the retropubic space, the window being large enough to pass two fingers. The retropubic space is then freed from adhesions.

Under careful finger control, the curved fascial anchor is passed from the vaginal to the suprapubic area. The tip of the instrument is pointed just above the periostium of the superior rami of the symphysis. It is strongly recommended to transfer the anchor as close to the pubic bone as possible in order to minimize suprapubic pain.

Keeping this guideline in mind, a fascial anchor having a No. 1 Prolene suture is inserted in the suprapubic area. After fixation of the anchor, the ends of the anchor's sutures are pulled on to verify that the anchor has been strongly fixated into the tissue. A total of two anchors are inserted. The free end of the Prolene sutures will be used to support the fascial sling.

A segment of sling 7 to 8 cm by 2 cms in size is then obtained. Various options are available for the sling material. The sling can be made from cadaveric or autologous fascia (from the abdominal wall or fascia lata). Or, if desired, the sling can be made from any FDA approved synthetic material.

One of the Prolene sutures is used to firmly anchor one end of the sling. Several passes of the needle over the tissue is recommended. It is important for the sling to slide freely from the suture.

Using a long beak right angle clamp, a tunnel is made underneath the vaginal wall at the level of the bladder neck. Using a free suture as a guide, the sling is transferred beneath the vaginal wall to the contralateral side. As an alternative in difficult cases, a transverse incision is made at the level of the bladder neck and the sling is transferred to the contralateral side.

In a similar fashion, the second Prolene suture in the contralateral side will include the other side of the sling, while ensuring that the sling can freely slide from the suture. Cystoscopy is performed in order to assure bladder integrity and good positioning of the sling. By the nature of the procedure, there is no need to check for ureteric efflux. A suprapubic catheter is inserted for drainage and its position is controlled during the cystoscopy.

The Prolene sutures are then tied sequentially after inserting a cystoscopy sheath into the urethra at a 30-degree angle. Alternatively, a clip applier can be used, obviating the need for suture ties. The vaginal wall is closed with a running 20 Vycryl suture. After two hours, the vaginal packing is removed and the suprapubic catheter is plugged. The patient is instructed to check post void residuals every 2-3 hours or as required by the urgency to urinate. The patient can be discharged home after 4-6 hours on a regular diet, oral antibiotics and pain medication. The patient can resume normal activities (walking, standing, sitting, etc.) as soon as they feel comfortable. Impact exercise or heavy lifting should be avoided for one month. The suprapubic catheter is removed as soon as the residuals of urine are less than 60 cc.

Vaginal Wall Sling Using Facial Anchors.

In a further invention, a vaginal sling procedure is provided herein for the treatment of stress incontinence in patients with mild to moderate cystocele (lateral defect only).

In accordance with the invention, under general, spinal or local anesthesia with controlled sedation, two oblique incisions are made in the anterior vaginal wall. The vaginal wall is dissected laterally over the periurethral fascia. Using Mayo scissors and pointing toward the ipsilateral shoulder, the retropubic space is entered in each side. The urethropelvic ligament is detached, creating a small window in the retropubic space sufficiently large to pass two fingers. The retropubic space is then freed from adhesions.

Under careful finger control, the curved fascial anchor is passed from the vaginal to the suprapubic area. The tip of the instrument is pointed just above the periostium of the superior rami of the symphisis. It is strongly recommended to transfer the anchor as close to the public bone as possible in order to minimize suprapubic pain.

A fascial anchor having a No. 1 Prolene suture is then inserted into the tissue of the suprapubic area. After the inserting the anchor into the tissue, the ends of the sutures are pulled down to ensure that the anchor has been securely fixed into to the tissue. A total of four anchors are fixed in the tissue, in all. The free end of the Prolene sutures will be used to support the anterior vaginal wall.

The first suture will include the perivesical fascia and medial edge of the urethropelvic ligament at the level of the bladder neck. The second suture will include the urethropelvic ligament (midurethral complex), the edge of the urethropelvic ligament, and the periurethral fascia.

The same maneuver is then performed in the contra lateral side.

Once these steps have been completed, cystoscopy is performed in order to ensure bladder integrity and good efflux of urine from the ureteric orifices. A suprapubic catheter is inserted for drainage and its position is controlled during the cystoscopy. The Prolene sutures are then tied sequentially after inserting a cystoscopy sheath into the urethra at a 30 degree angle. Alternatively, a clip applier can be used, obviating the need for suture ties.

The vaginal wall is then closed with a running 2-0 Vycryl suture. After two hours, the vaginal packing is removed and the suprapubic catheter is plugged. The patient is instructed to check post void residuals every 2-3 hours or as required by the urgency to urinate. The patient can be discharged home after 4-6 hours on regular diet, oral antibiotics and pain medication. The patient can resume normal activities (walking, standing, sitting, etc.) as soon as they feel comfortable. Impact exercise or heavy lifting should be avoided for one month. The suprapubic catheter is removed as soon as the residuals of urine are less than 60 cc.

Supporting the Vaginal Cuff During Vaginal Hysterectomy Using Fascial Anchors.

In a further invention, a technique for supporting the vaginal cuff during vaginal hysterectomy using fascial anchors is also provided herein. This technique is recommended for closure of the vaginal cuff at the time of vaginal hysterectomy for prolapse. It is aimed at preventing prolapse of the vaginal cuff, preservation of vaginal depth and restoration of the normal vaginal axis.

Once the hysterectomy has been completed, marking sutures are left in place at the sacrouterine-cardinal complex, uterine artery and broad ligaments, and the peritoneal sac is left open. A large moist pad is inserted in the peritoneal sac and retracted with a deep right angle retractor. The small bowel or distal colon is pushed away from the operating field.

A deep posterior retractor is inserted to displace the rectum to the left, exposing the right pararectal area. Sliding a finger over this space the soft levator musculature is felt, and just posteriorly, the hard surface of the coccigeus muscle and sacrospinous ligament, running between the ischial spine and the sacrum.

Using a straight fascial anchor and under finger control, two absorbable anchors are inserted through the right sacrospinous ligament, 2-3 cm medial to the ischial spine. The strength of the anchor is tested by a strong pull on the sutures that are preloaded. The sutures should slide freely.

At the deepest point of the vagina, one free end of the suture is used for threading through a good sized segment of the vaginal wall. This free end of the suture is then transferred to the vaginal lumen. The other end of the suture is also threaded through the vaginal lumen, at a distance of 1 to 2 cm from the prior suture.

Two sequential purse string sutures of No. 1 Vycryl are then used to close the peritoneal cavity. The suture includes the pre-rectal fascia, the sacrouterine and cardinal ligaments, and the perivesical area. Alternatively, a Dexon mesh can be included with the last suture to reinforce the closure of the cul de sac. The sutures are tied and the excess of peritoneum is excised.

The broad ligament sutures are then tied together in the midline. Then the uterine artery sutures and the sacrouterine ligament sutures are cut. The vaginal cuff is closed in a transverse fashion with running locking sutures. The rest of the vaginal reconstruction is performed as indicated.

Repair of Vaginal Vault Prolapse Using Fascial Anchors

In a further invention, a technique for repair of vaginal vault prolapse using fascial anchors is also provided herein. A similar technique can be used to support the uterus and vaginal cuff in cases of severe vault prolapse. No hysterectomy or opening of the peritoneum is required.

This surgery is similar to the enterocele repair. A vertical incision is made over the posterior and superior vaginal wall. The dissection is carried out laterally to enter the extraperitoneal pararectal space, toward the coccigeus muscle (above levators, beneath peritoneum and lateral to the rectum). The sacrospinous ligament is felt as it attaches to the ischial spine. Two fascial anchors are applied 2-3 cm medial from the spine. The end to the sutures is used to anchor the vaginal wall in a similar fashion, as described above. After closing the vaginal wall, the sutures are tied, making sure that the vaginal wall slides easy to the anchoring point.

Having described this invention with regard to specific embodiments, it is to be understood that the description is not meant as a limitation since further modifications and variations may be apparent or may suggest themselves to those skilled in the art. It is intended that the present application cover all such modifications and variations.

What is claimed is:

1. A surgical procedure for treating a patient, comprising the steps of:
making at least one incision; providing a sling having at least one soft tissue anchor; and
using a tissue anchor inserter to place the at least one soft tissue anchor initially through the at least one incision and then into a patient's soft tissue;
wherein the step of placing the at least one soft tissue anchor into a patient's soft tissue comprises placing the at least one soft tissue anchor into the patient's sacrospinous ligament,
associating the at least one soft tissue anchor with a needle of the soft tissue anchor inserter and activating a release on the soft tissue anchor inserter to deploy the at least one soft tissue anchor from the needle and into the patient's soft tissue, and
further comprising the step of providing a plunger capable of axial movement within the needle of the soft tissue anchor inserter wherein activating the release axially moves the plunger which deploys the at least one soft tissue anchor from the needle.

2. A surgical procedure according to claim 1 wherein the step of providing a plunger capable of axial movement within the needle of the soft tissue anchor inserter to deploy the at least one soft tissue anchor from the needle comprises moving the plunger axially toward the soft tissue anchor to deploy it from the needle.

3. A surgical procedure according to claim 1 wherein the step of associating the at least one soft tissue anchor with the needle further comprising the step of disposing the at least one soft tissue anchor to an anchor guide on the end of the needle prior to deployment.

4. A surgical procedure according to claim 1 further comprising the step of providing a safety on the tissue anchor inserter to prevent release of the at least one soft tissue anchor from the tissue anchor inserter until desired.

5. A surgical procedure according to claim 1, wherein the method comprises treating urinary incontinence.

6. A surgical procedure according to claim 1, wherein the method comprises treating cystocele in a female patient.

7. A surgical procedure according to claim 1, wherein the method comprises supporting vaginal tissue.

8. A surgical procedure according to claim 1, wherein the method comprises treating vaginal vault prolapse.

9. A surgical procedure for treating a patient, comprising the steps of:
making at least one incision; providing a sling having at least one soft tissue anchor; and
using a tissue anchor inserter to place the at least one soft tissue anchor initially through the at least insertion and then into a patient's soft tissue;
wherein the step of placing the at least one soft tissue anchor into a patient's soft tissue comprises placing the at least one soft tissue anchor into the patient's first sacrospinous ligament and implanting another soft tissue anchor into the patient's second sacrospinous ligament with the sling extending between the first and second soft tissue anchors to support an organ or tissue.

10. A surgical procedure according to claim 9, wherein the step of using a soft tissue anchor inserter further comprises the step of associating the at least one soft tissue anchor with a needle of the soft tissue anchor inserter and activating a release on the soft tissue anchor inserter to deploy the at least one soft tissue anchor from the needle and into the patient's soft tissue.

11. A surgical procedure according to claim 10 further comprising the step of providing a plunger capable of axial movement within the needle of the soft tissue anchor inserter wherein activating the release axially moves the plunger which deploys the at least one soft tissue anchor from the needle.

12. A surgical procedure according to claim 11 wherein the step of providing a plunger capable of axial movement within the needle of the soft tissue anchor inserter to deploy the at least one soft tissue anchor from the needle comprises moving the plunger axially toward the soft tissue anchor to deploy the soft tissue anchor from the needle.

13. A surgical procedure according to claim 10 wherein the step of associating the at least one soft tissue anchor with the needle further comprising the step of disposing the at least one soft tissue anchor to an anchor guide on the end of the needle prior to deployment.

14. A surgical procedure according to claim 10 further comprising the step of providing a safety on the tissue anchor inserter to prevent release of the at least one soft tissue anchor from the tissue anchor inserter until desired.

15. A surgical procedure according to claim 9, wherein the method comprises treating urinary incontinence.

16. A surgical procedure according to claim 9, wherein the method comprises treating cystocele in a female patient.

17. A surgical procedure according to claim 9, wherein the method comprises supporting vaginal tissue.

18. A surgical procedure according to claim 1, wherein the method comprises treating vaginal vault prolapse.

* * * * *